United States Patent [19]
Andrews

[11] Patent Number: 5,807,103
[45] Date of Patent: Sep. 15, 1998

[54] DENTAL IMPRINT PAD WITH STEM FOR MOUNTING TO A BITE FORK

[76] Inventor: Lawrence F. Andrews, 6101 La Jolla Mesa Dr., La Jolla, Calif. 92037

[21] Appl. No.: 673,737

[22] Filed: Jun. 27, 1996

[51] Int. Cl.[6] ....................................... A61C 9/00
[52] U.S. Cl. ................. 433/71; 433/214; 433/48
[58] Field of Search .................. 433/37, 40, 42, 433/47, 48, 71, 214

[56] References Cited

U.S. PATENT DOCUMENTS

| | | | |
|---|---|---|---|
| 685,868 | 11/1901 | Reavis | 433/48 X |
| 2,313,535 | 3/1943 | Glitzke | 433/71 |
| 3,390,458 | 7/1968 | Lytton | 433/40 |
| 3,473,225 | 10/1969 | Deuschle et al. | 433/48 |
| 3,602,993 | 9/1971 | Kenney | 433/40 X |
| 4,693,683 | 9/1987 | Lee | 433/42 X |
| 5,059,120 | 10/1991 | Lee | 433/37 |
| 5,154,609 | 10/1992 | George | 433/214 X |
| 5,176,515 | 1/1993 | Andrews | 433/24 |

*Primary Examiner*—Nicholas D. Lucchesi
*Attorney, Agent, or Firm*—Gary Cary Ware Freidenrich

[57] ABSTRACT

A dental impression article made of a dental imprint material is for use with a bite fork having one or more planar members, each planar member having one or more holes. The dental imprint article includes a pad of dental imprint material that may be molded when heated. The pad of dental imprint material is for engaging a surface of planar member of the bite fork and includes a stem of dental imprint material that engages the bite fork. The stem is received through a hole in the bite fork planar member, heat is applied, and the stem is deformed, spreading beyond the hole on another surface of the planar member. When the apparatus is cooled, the dental imprint article is retained on the bite fork for use.

20 Claims, 1 Drawing Sheet

DENTAL IMPRINT PAD WITH STEM FOR MOUNTING TO A BITE FORK

BACKGROUND OF THE INVENTION

1. Field of the Invention

This invention relates to orthodontic instrumentation used to take dental imprints, and more particularly to a dental imprint pad for use with a bite fork.

2. Description of the Related Art

Dentists, orthodontists, oral surgeons and plastic surgeons utilize accessories to obtain dental impressions for the purpose of making dental casts. When mounted on articulators, the dental casts show the relationships of a patient's dental anatomy that must necessarily be understood in order to devise a plan that may involve orthodontically or surgically altering the position of the teeth and jaws of the patient.

A dental treatment method and apparatus that embrace an articulator are disclosed in detail in U.S. Pat. No. 5,176,515, which is incorporated herein in its entirety by this reference.

The method and apparatus of the '515 patent both utilize a bite fork for obtaining dental imprints. Typically, such a bite fork is a rod connected to a bite plate that includes, flat arch-shaped section. The arch-shaped section provides two surfaces on which dental imprint material is placed. The bite fork, with the added dental imprint material is warmed, then inserted between the upper and lower teeth. The bite plate is pressed against the upper teeth which imprint in the softened dental imprint material. Once cooled to mouth temperature the material is removed leaving the permanent imprint of the biting surfaces of the teeth.

U.S. Pat. No. 5,059,120 disclosed a structure, a composition, and a method of manufacturing dental imprint pads for use on bite forks. The dental imprint pads of the '120 patent include a strip of thin material having two sides, an adhesive covering a first side of the strip of material, and a dental imprint material attached to the second side of the strip. The dental imprint pad of '120 patent is attached to a bite fork by the adhesive covering on the first side of the strip, which orients the dental imprint material outwardly in order that it may receive imprints of the biting surfaces of a patient's upper teeth.

The dental imprint pads of the '120 patent may fail to adhere to the surfaces of a bite fork. For example, with age, the stickiness of the adhesive material may attenuate. Further, the adhesive material may not be retained on wet bite fork surfaces. In such cases, the dental imprint pads may not attach to bite fork surfaces, or, if they do attach, may be loosened and disattached during the taking of dental imprints.

Further, the dental imprint pads of the '120 patent require a complex, multi-step manufacturing process in which a laminated sheet is pre-cut, coated with an adhesive material, and then reciprocated for receiving small mounds of dental imprint material.

Manifestly, the state of the art would be advanced by the provision of dental imprint tabs for use with a bite fork which can be easily and reliably attached to its bit plate portion thereto and inexpensively manufactured.

SUMMARY OF THE INVENTION

This invention is based upon the inventor's critical observation that a dental imprint pad with a stem can be easily and reliably adjoined to a bite fork by reception of the stem through a hole in the bite fork, heating of the bite fork and dental imprint pad, and deformation of the stem to engage the bite fork.

Further, the inventor has realized that provision of a dental imprint pad having a disk- or button-shaped member made of dental imprint material and a stem integrally formed therewith supports a very simple and inexpensive manufacturing process in which a molding tray with a plurality of pre-shaped wells receives, in each well, molten dental imprint material which hardens within the well, and is shaped by the well to the disk- and stem structure.

Such a dental imprint article has innately in its composition and structure the means for being retained on a bite fork without the need for adhesive.

Further, such a dental imprint article may be easily manufactured in a process that utilizes only a molding tray and molten dental imprint material.

Other features and advantages of this invention will appear from the following description and drawings which set forth, for the purpose of illustration and example, one preferred embodiment of the invention.

DETAILED DESCRIPTION OF THE PREFERRED EMBODIMENTS

Figure 1:
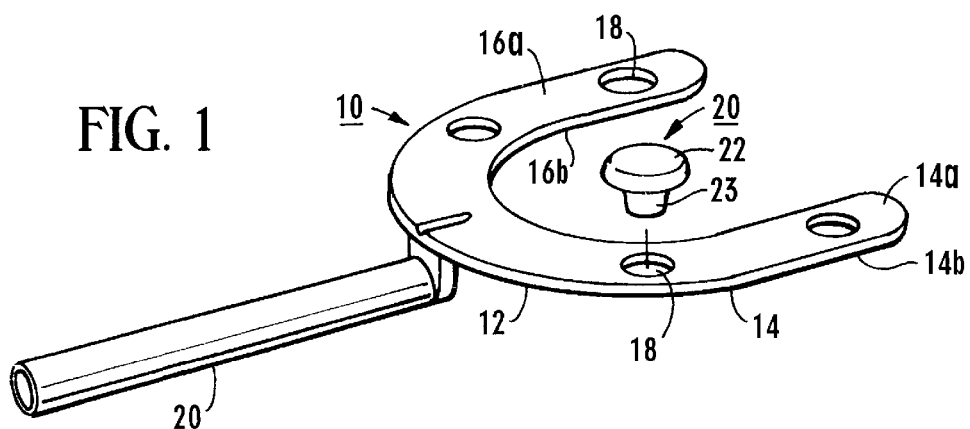
FIG. 1 illustrates an example of a bite fork and a dental imprint pad oriented with respect to a hole in the bite fork for inserting it therein.

FIG. 1 shows a bite fork indicated generally by 10. The bite fork 10 is used by, for example, dentists in connection with dental, orthodontic, or surgical treatment. An example of such use is explained in detail, for example, in the incorporated '515 patent. The bite fork 10 includes a bite plate 12. The bite plate 12 is an example and illustration of a bite plate which, as those skilled in the art will realize, may come in many configurations and shapes. Nevertheless, the bite plate 12 is a thin, flat, arch-shaped piece having two legs 14 and 16. Each of the legs 14 and 16 is a thin, flattened extension that has two oppositely-directed surfaces indicated by 14a and 14b for the leg 14 and by 16a and 16b for the leg 16.

One or more holes may be provided in the bite plate. For example and illustration, the bite plate 12 has four holes 18 arranged as illustrated in FIG. 1 such that there are generally two holes 18 in each of the legs 14 and 16. Each of the holes 18 opens from one surface to the other surface of a respective leg. A dental imprint pad 20 embodying this invention is used with the bite fork 10. The dental imprint pad 20 is an integral piece formed from a dental imprint material, such as sealing wax, and has a disk- or button-shaped tab 22 and, integral therewith, a stem 23 extending from a surface of the tab 22.

Preferably, the disk-shaped portion is circular, having a diameter $d_1$. This dimension is greater than the diameter $d_2$ of the holes 18 in the bite plate. The stem has a width dimension $d_3$ that is smaller in magnitude than $d_1$.

Preferably, for a frusto-conically shaped stem, the width dimension of the stem would be the cross-section where the stem joins the disk-shaped portion. At this location, the diameter $d_3$ of the stem has its greatest magnitude. Of course the stem may have other shapes that may be convenient. For example the stem may be a right cylinder in which $d_3$ is constant. Whatever the shape is chosen for the stem, its width dimension $d_3$ must be slightly smaller than the diameter $d_2$ of the holes in the bite plate. Thus, $d_1 > d_2 > d_3$.

Figure 2:
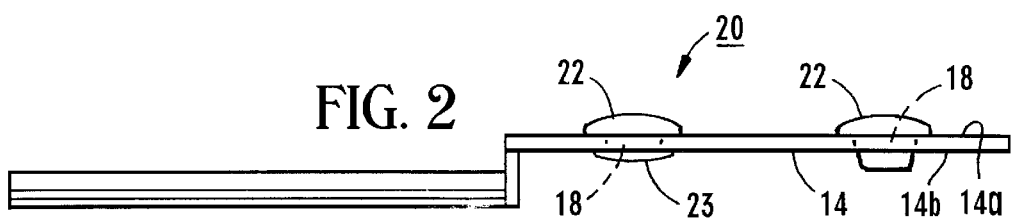
FIG. 2 is a side view that illustrates the dental imprint pad mounted to the bite fork.
Figure 3:
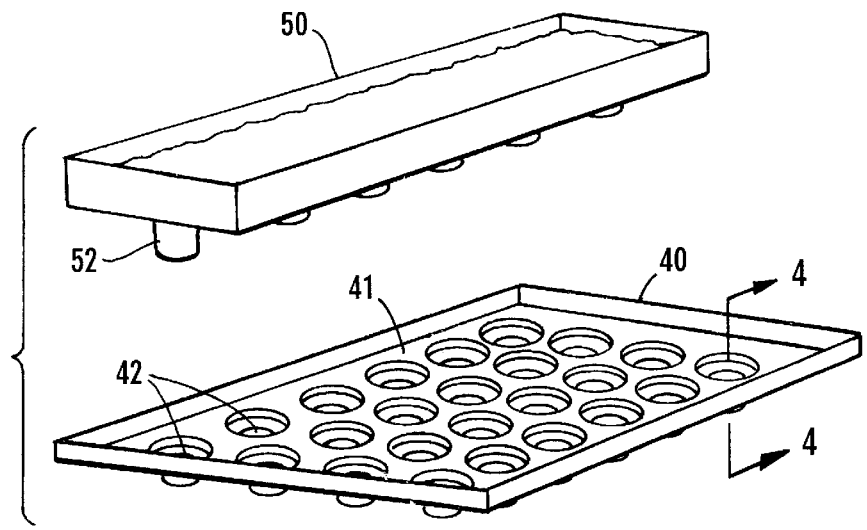
FIG. 3 shows a molding tray with a plurality of shaped wells for manufacturing, shipping and distributing dental imprint pads.

As illustrated in FIGS. 1 and 2, a dental imprint pad 20 is mounted to the bite plate 12 by inserting the stem 23 through the hole 18 so that the tab 22 rests on one surface 14a of the leg 14 of the bite plate 12. In FIG. 2, two dental imprint pads 20 are shown mounted to the leg 14. According to the preferred embodiment, and in illustration of the invention, each of the dental imprint pads 20 has its disk- or button-shaped tab 22 resting on the upper surface 14a of the leg 14, while the stem 23 of each dental imprint pad 20 extends through a respective hole 18. The bite fork 10 with dental imprint pads 20 inserted thereto may be heated in order to soften the dental impression material of which the dental imprint pads are made. When soft enough, a dental imprint pad 20 can be retained on a surface of the bite plate by deforming its stem so that the stem assumes a partially flattened configuration with edges that extend beyond the hole 18 through which it is inserted, along a lower surface of the bite plate. This is shown in FIG. 2, by the mass 24 which results from deformation of the stem 23'. When the bite fork with the mounted dental imprint pads cools, the stems of the dental imprint pads retain their (now deformed) states, which rivets the dental imprint pads to the bite fork.

The shape and structure of the dental imprint pad 20 that is shown in FIGS. 1 and 2 is exemplary and illustrative of the invention. Importantly, the pad and stem form an integral unit that can be shipped and used as a single piece. Moreover, while the pad is shown as being generally disk- or button-shaped, other shapes may be useful. Further, the stem of the dental imprint pad is shown as having a generally frusto-conical shape. Although this shape is particularly well adapted for engaging with the holes of the bite plate, other shapes, such as a right cylinder may be used.

With dental imprint pads mounted as set forth in the explanation of FIGS. 1 and 2, a bite fork is put to its intended use which may be understood, for example, by reference to the description in the '515 patent. When use is completed, the dental imprint pads may be removed from a bite fork by cutting the now enlarged stem and lifting off the pads, after which the bite fork can be used again in the manner contemplated by this invention.

Figure 4A:
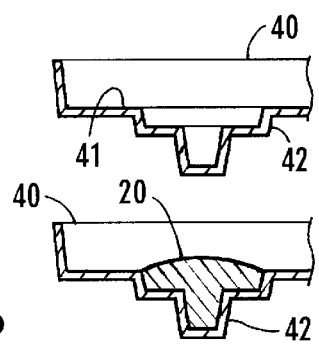
FIGS. 4A and 4B show, respectively, a side sectional view of a portion of the molding of FIG. 3 before and after receiving the molten dental imprint material for formation of a dental imprint pad according to the invention.

The ease with which the dental imprint pads of this invention may be manufactured is illustrated in FIGS. 3, 4A, 4B and 5. Relatedly, a molding tray 40 may be shaped to include a generally planar surface 41 that defines the openings of plurality of shaped molding wells 42. The molding wells generally have the elevational cross-sectional shape of the dental imprint pads described above. This is illustrated in FIG. 4A which shows the side sectional view of the molding tray 40 taken at one of the wells 42. In the illustrative embodiment, the molding tray 40 includes twenty-four molding wells 42 in a 6×4 array. The preferred embodiment of the molding tray 40 is made from a molded plastic material.

Manufacture of the dental imprint pads according to the invention includes provision of a molding tray, such as the molding tray 40, having a plurality of molding wells, such as the molding wells 42, formed therein. A dispenser 50 holds a volume of melted dental imprint material and drops a metered amount into each molding well as the molding well is registered beneath an applicator 52 of the dispenser. Preferably, the manufacturing process includes incrementally repositioning the molding tray 40 beneath the applicator 52, or providing a multiple-jet applicator that can dispense metered amounts of melted dental imprint material into an entire row or column of molding wells simultaneously.

Figure 4B:
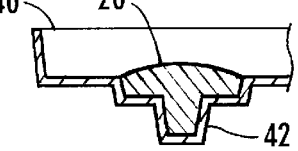
Figure 5:
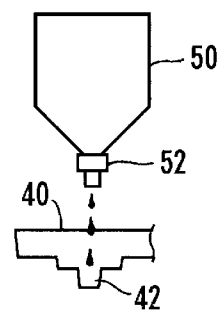
FIG. 5 shows a manufacturing set up for fabricating dental imprint pads according to the invention.

When received in the molding wells 42, the melted dental imprint material cools and hardens into the preferred shape of the dental imprint pad, as is illustrated in FIG. 4B. Here the dental imprint pad 20 is shown in one of the wells 42 of the molding tray 40. Once the dental imprint material has cooled and hardened into individual dental imprint pads, the molding tray 40 may be covered to retain the dental imprint pads 20 in the molding wells 42 for shipment, storage, and distribution. Alternatively, dental imprint pads can be removed from molding trays after formation and shipped in bulk.

After distribution to end users, the cover may be removed from the molding tray 40 and individual dental imprint pads removed therefrom for use as described above.

This invention may be practiced according to the disclosed embodiment. However, the embodiment is merely exemplary illustrative and many modifications and variations can be made to it without departing from the spirit of this invention, as defined in the following claims.

I claim:

1. A dental imprint article for use with a bite fork having one or more holes, comprising:

a pad of dental imprint material for engaging a surface of the bite fork; and dental imprint material means formed on the pad for engaging a hole in the bite fork.

2. The dental imprint article of claim 1, wherein the pad is generally disk-shaped.

3. The dental imprint article of claim 1, wherein the means is a stem and the pad and stem form an integral unit.

4. The dental imprint article of claim 3, wherein the pad is generally disk-shaped and has a diameter $d_1$ for engaging a hole in a bite fork having a dimension $d_2$ of width, where $d_1 > d_2$.

5. The dental imprint article of claim 4, wherein the stem is a generally elongate member having a dimension $d_3$ of width, where $d_1 > d_2 > d_3$.

6. The dental imprint article of claim 5, wherein the stem is substantially frusto-conical.

7. The dental imprint article of claim 3, wherein the stem is substantially frusto-conical.

8. The dental imprint article of claim 3, wherein the stem is substantially cylindrical.

9. A combination for making dental imprints, comprising:

a bite fork with at least one planar member;

a plurality of holes opening through the at least one planar member;

a plurality of dental imprint articles, each including a pad of dental imprint material for engaging a surface of the at least one planar member and a stem of dental imprint material formed on the pad for engaging a hole.

10. The combination of claim 9, wherein each pad is generally disk-shaped.

11. The combination of claim 10, wherein each stem is substantially frusto-conical.

12. The combination of claim 10, wherein each stem is substantially cylindrical.

13. The combination of claim 9, wherein each pad and stem form an integral unit.

14. The combination of claim 13, wherein each pad is generally disk-shaped and has a diameter $d_1$, and each hole has a dimension $d_2$ of width, where $d_1 > d_2$.

15. The combination of claim 14, wherein each stem is a generally elongate member having a dimension $d_3$ of width, where $d_1 > d_2 > d_3$.

16. The combination of claim 15, wherein each stem is substantially frusto-conical and the hole is substantially circular.

17. A combination for storing dental articles, comprising:
   a holding tray with a plurality of wells;
   a plurality of dental imprint articles, each dental imprint article in a respective well of the plurality of wells;
   each dental imprint article of the plurality of dental imprint articles including:
      a pad of dental imprint material for engaging a surface of a bite fork, and
      a stem of dental imprint material formed on the surface for engaging a hole in the bite fork.

18. The combination of claim 17, wherein each pad is generally disk-shaped.

19. The combination of claim 17, wherein each pad and stem form an integrated unit.

20. The combination of claim 17, wherein each stem is substantially frusto-conical.

* * * * *